US00PP15647P2

(12) United States Plant Patent
Swartz et al.

(10) Patent No.: US PP15,647 P2
(45) Date of Patent: Mar. 8, 2005

(54) RASPBERRY PLANT NAMED 'JACLYN'

(50) Latin Name: *Rubus ideaus L.*
Varietal Denomination: Jaclyn

(75) Inventors: Harry J. Swartz, Laurel, MD (US); Joseph A. Fiola, Keedysville, MD (US); Herbert D. Stiles, Blackstone, VA (US); Brian R. Smith, River Falls, WI (US)

(73) Assignees: University of Maryland, Riverdale, MD (US); University of Wisconsin, River Falls, WI (US); Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 10/644,083

(22) Filed: Aug. 20, 2003

(51) Int. Cl.[7] ..... A01H 5/00
(52) U.S. Cl. ..... Plt./204

(58) Field of Search ..... Plt./204

(56) References Cited

U.S. PATENT DOCUMENTS

| | | | |
|---|---|---|---|
| PP10,411 | P | 5/1998 | Swartz et al. |
| PP10,412 | P | 5/1998 | Swartz et al. |
| PP12,350 | P2 | 1/2002 | Swartz et al. |

*Primary Examiner*—Bruce R. Campbell
*Assistant Examiner*—S B McCormick-Ewoldt
(74) *Attorney, Agent, or Firm*—Dykema Gossett PLLC

(57) ABSTRACT

The present invention is a new and distinct primocane fruiting red raspberry cultivar named 'Jaclyn', which is capable of producing fruit much earlier than that of the standard cultivars. The cultivar is characterized by a vigorous suckering ability and its consistently large, dark, long conic and very symmetrical fruit. Fruit seldom sunscalds in the mid-Atlantic states when grown under standard irrigation and fertilization practices. Fruit aroma is very full, and fruit quality is excellent through even high temperatures. Fruit separation can be difficult in cooler weather.

10 Drawing Sheets

FIELD OF THE INVENTION

This invention concerns a new and distinct cultivar of primocane fruiting raspberry plant with a botanical name of *Rubus ideaus* L.

DESCRIPTION OF RELATED PRIOR ART

Several cultivars of primocane fruiting (commonly known as "fall bearing") raspberry plant are known. For instance, raspberry cultivars named 'Anne', 'Caroline' and 'Josephine' have been described in U.S. Plant Pat. Nos. 10,411, 10,412 and 12,173, respectively. The new and distinct cultivar of the present invention is a raspberry plant named 'Jaclyn'. This new and distinct cultivar of the present invention differs from 'Anne' in bearing red fruit, while 'Anne' bears golden fruit. Compared with 'Anne', 'Jaclyn' produces more root and crown-suckers and has significantly earlier ripeness period for the primocane fruit, which is usually more free from rot and sunscald in the field. 'Jaclyn' can be distinguished from 'Caroline' in that 'Jaclyn' fruit is larger, darker and more cohesive, produced one to two weeks earlier on primocanes, and has less fruit rot but the plant will have more late season leaf rust. 'Jaclyn' leaves do not regularly curl in high sun and warm temperatures as 'Caroline'. 'Jaclyn' and 'Josephine' are both large fruited primocane fruiting red raspberry cultivars, but 'Jaclyn' can be distinguished from 'Josephine' in that 'Jaclyn' is fruit is produced on primocanes a month before 'Josephine' and 'Jaclyn' fruit is conic, sweet and dark colored when fully ripe, compared to the round, lighter colored, 'Josephine' fruit.

ORIGIN OF THE NEW CULTIVAR

The new cultivar of fall bearing red raspberry originated from a controlled cross at the University of Maryland Greenhouses in College Park, Md. The cross OBC-f1 (unpatented)×'Caroline' (U.S. Plant Pat. No. 10,412) and was made in the winter of 1996 and designated "EG" as the breeder code for the cross. OBC-f1 is a selection from the cross KP-2×KAS-1. KP-2 (unpatented) is from a cross of CFO-1×GEN-1. CFO-1 (unpatented) is a cross of 'Southland' (unpatented)×'Willamette' (unpatented). GEN-1 (unpatented) is a cross of an F2 of *R. pileatus*×SCRI 8216B6 (unpatented). KAS-1 (unpatented) is a cross of GDF-3 (unpatented)×*R. stellarcticus* 'Linda' (unpatented). GDF-3 is a cross of selection SCRI 52B6 black-purple raspberry (unpatented)×'Autumn Bliss' (U.S. Plant Pat. No. 6,597). SCRI designated selections are by courtesy of the Scottish Crop Research Institute, Invergowrie, Scotland, United Kingdom (via. Dr. Derek Jennings). The other selections are from the University of Maryland at College Park; Rutgers University of New Brunswick, N.J.; Virginia Polytechnic Institute and State University, Southern Piedmont Agricultural Research and Education Center at Blackstone; and the University of Wisconsin at River Falls cooperative breeding program. This year of crossing was designated: "Q" as part of the University of Maryland at College Park; Rutgers University of New Brunswick, N.J.; Virginia Polytechnic Institute and State University, Southern Piedmont Agricultural Research and Education Center at Blackstone; and the University of Wisconsin at River Falls cooperative breeding program. The clone was first selected in 1998 at the Rutgers Fruit Agricultural Experiment Station at Cream Ridge, N.J. and was therefore designated "-f1". Thus, the complete breeding designation was "QEG-f1".

SUMMARY OF THE NEW CULTIVAR

This application relates to a new and distinct red fruited, primocane fruiting, raspberry cultivar, botanically known as

*Rubus ideaus* L. The following characteristics are outstanding:

1. Production of fruit on primocanes which is earlier than all other commercially grown cultivars worldwide, except 'Polana', which ripens in the same season, but sunscalds, and is much smaller than 'Jaclyn'.
2. In all the areas of test of this selection, the fruit is larger than all cultivars known to us, except sister seedlings 'Anne' (U.S. Plant Pat. No. 10,411) and 'Josephine' (U.S. Plant Pat. No. 12,173) from the above cooperative breeding program and 'Ruby' (syn. 'Watson' U.S. Plant Pat. No. 7,067), a much later ripening cultivar from New York. Fruit size and fruit color are not severely reduced by temperatures between 80 and 90 F.
3. It is more productive than primocane fruiting cultivars tested in our area, except for 'Caroline' which is the highest yielding primocane bearing red raspberry in the eastern U.S. 'Caroline' fruit size is much lower in all climates, especially when grown in warmer regions.
4. In warmer areas, or in unheated greenhouse "tunnels", 'Jaclyn' buds on the mid section of primocanes, that is, below the apical fruiting zone, will break and produce a second crop after the initial crop has been harvested from the tops of the canes.

These characteristics make 'Jaclyn' suitable as an mid-summer primocane fruiting type for California, the Mid-Atlantic States and in the southern Mid-West. The second primocane crop will ripen in September through October in a less concentrated ripening period. In cooler areas with less than 2500 growing degree days (base 50 F.), 'Jaclyn' primocane fruit ripens in September, making it sufficiently early to use as a primocane bearer for almost all agricultural regions in the United States.

As this cultivar was tested as a primocane bearer, meaning all overwintering canes were removed, no claim is made regarding its cold hardiness or chilling requirement. The ready production of a second primocane crop, on buds basal to the fruit producing region on the primocanes, indicates these buds do not have a chilling requirement as they do in other cultivars, e.g. 'Heritage' (unpatented).

The following characteristics are useful in distinguishing this cultivar from other cultivars and can be useful for cultivar identification.

1. The non-tissue culture produced plants produce primocanes which terminate in flower clusters, usually by the $15^{th}$ node. By comparison, 'Caroline' and 'Heritage' produce fruit, on average, at the $25^{th}$ and $29^{th}$ nodes, respectively. Tissue culture produced 'Jaclyn' plants produce flowers, on average, at the $21^{st}$ node.
2. The fruit is long conic with a cavity about 30% of the fruit diameter, compared to the round conic 'Josephine', which has a cavity 40% of the fruit diameter. Fruit diameter to length ratio is usually less than 3:4, except on smaller fruit. Fruit is very cohesive and red to red-purple when overripe and very symmetrical. Like 'Josephine', but unlike 'Polana' which ripens in the same season, drupelets will often tear in half before separating from the neighboring drupelets.
3. The fruit is highly symmetrical, has an even collar and has a very slight amount of pubescence when ripe.
4. Primocanes, petioles and leaf veins are light green (Royal Horticultural Society color plate No 144C) with a slight red blush on the apical leaves and stem (Royal Horticultural Society color plate No 182C) and only a moderate amount of characteristic long red colored (Royal Horticultural Society plate 183B) thorns per node, with a 1 mm diameter circle of grayed purple coloration (Royal Horticultural Society plate 182C) at the base of the thorns.
5. Flowers are typically 1–3 weeks earlier to initiate ripening on primocanes than 'Caroline' (U.S. Plant Pat. No. 10,412), 'Heritage' (unpatented), new standards for fall production in the United States. Flowers on primocanes begin to appear during the first week of July in the Mid-Atlantic states. This initial flowering will continue for a month to six weeks. Individual fruit will ripen approximately 23 days after pollination in the late July to early September. Fruit production is similarly earlier than all other cultivars known to use that are grown in the Mid-Atlantic states. 'Polana' has a similar ripening period, but it is not grown in this area as fruit size is very small.
6. 'Jaclyn' primocanes will readily break buds subtending the apical fruiting truss when most of the fruit has been picked or has abscised. These buds, usually two per cane, will produce a second primocane crop in areas with a sufficient growing season.
7. A larger production (41–44%) of the primocane nodes of 'Jaclyn' are fruitful, compared to less than 29% for the cultivars 'Heritage', 'Josephine' and 'Caroline'.
8. 'Jaclyn' can also be distinguished by two negative characteristics. Fruit is difficult to remove in cooler areas and in warmer areas, the plant is susceptible to late season leaf (yellow) rust.

BRIEF DESCRIPTION OF THE PHOTOGRAPHS

The accompanying photographs show typical characteristics of the new variety:

DESCRIPTION OF THE NEW CULTIVAR

The following is a detailed description of the new cultivar, including fruit production, together with the cultivar's morphological characteristics. The characteristics of the cultivar were compared with other standards used in the Mid-Atlantic Region of the U.S. The description is based on information provided by cooperating scientists from plants grown in fields at Hurlock, Md., Colt's Neck, N.J., Oakland, Md., Mt. Airy, Md., Kent, England, and from plants grown in the greenhouses at College Park, Md.

Figure 1:
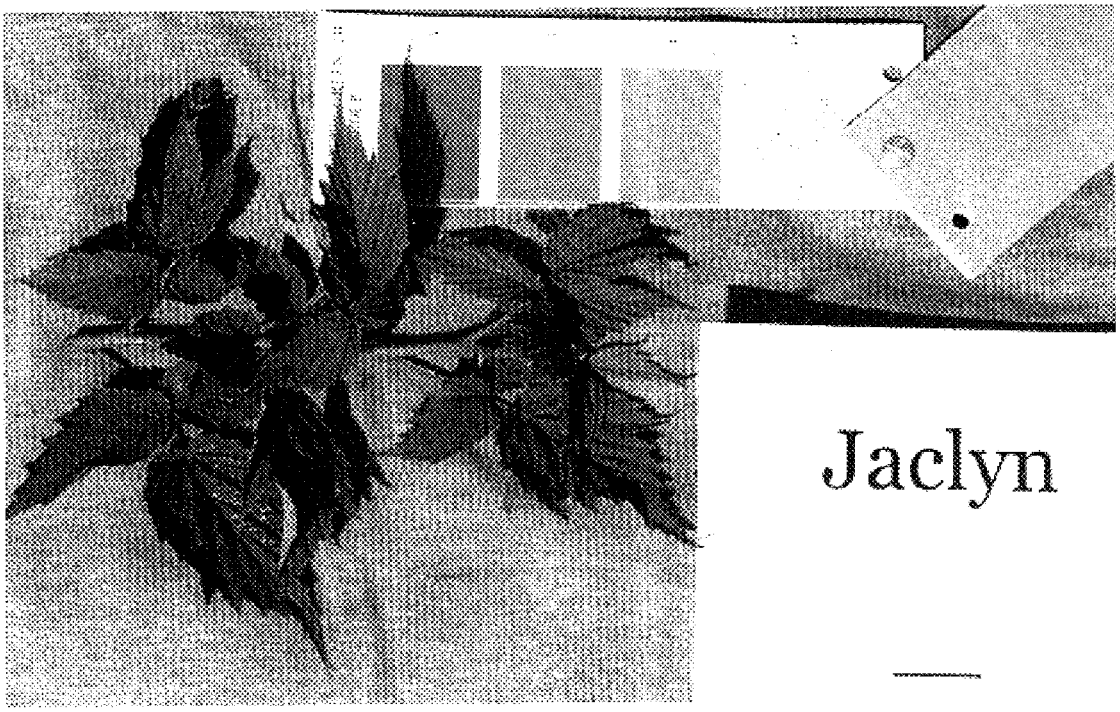
FIG. 1 shows a 'Jaclyn' primocane in early growth, with Royal Horticultural Society color plate No. 144.
Figure 2:
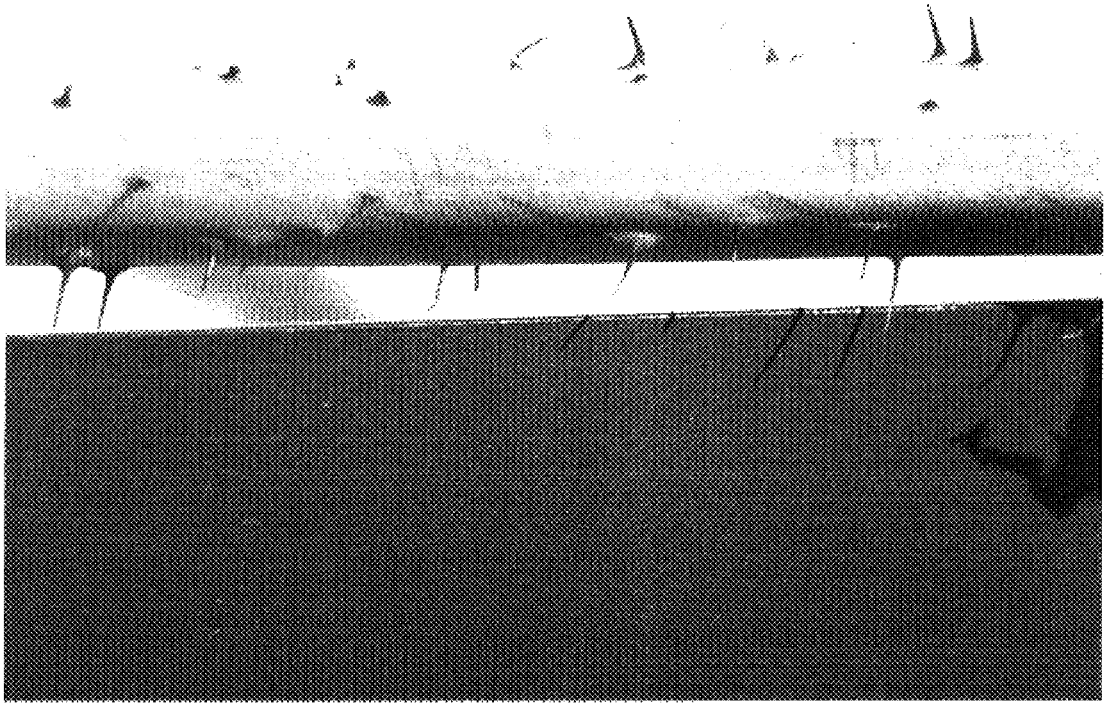
FIG. 2 shows the color, shape and density of thorns on a 'Jaclyn' primocane and Royal Horticultural Society color plate No. 183B.
Figure 3:
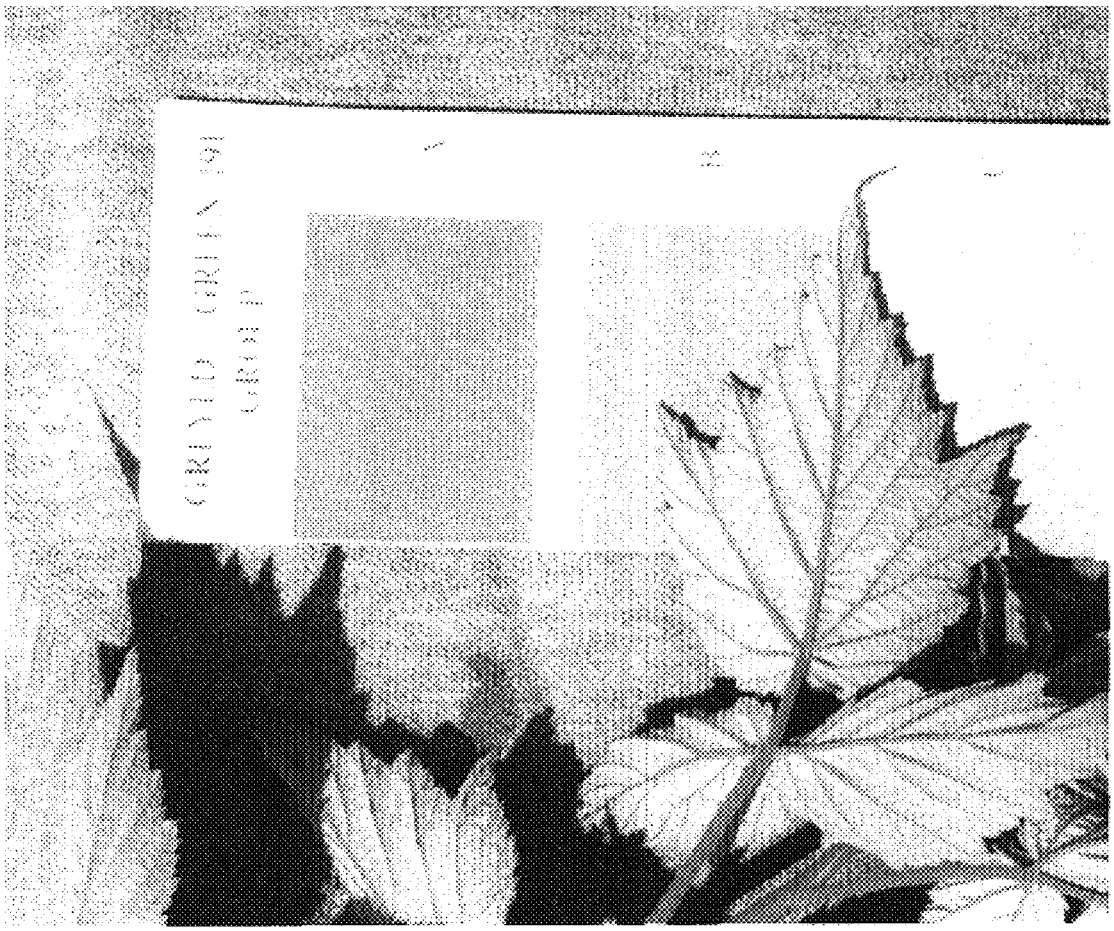
FIG. 3 shows the underside of a 'Jaclyn' leaf, and a Royal Horticultural Society color plate No. 191.

'Jaclyn' produces a moderately high number of root- and crown-suckers (approximately 6 per foot of row), more than 'Anne' and 'Josephine', but similar to 'Caroline' and 'Heritage'. During the growing season, canes are light green colored (Royal Horticultural Society color plate No. 144C) with a slight gray purple blush (Royal Horticultural Society plate No. 182C) in full sun (FIG. 1) Canes are usually unbranched and erect by the second year of a plant's growth. Total node number per cane is 26 for adult plant to 36 for rejuvenated tissue culture produced first year plants. By comparison, 'Heritage' produces 39 nodes per cane, 'Caroline' produces 36 nodes per cane on tissue culture produced first year plants and 'Josephine' produces 45 to 48 nodes per cane, on older adult or tissue culture produced first year plants. Growth is moderately vigorous, reaching on average 4 feet in full sun, or 5 feet in crowded conditions or in tunnels. Thorns are moderate in density: 24.8 per node at the base of the primocane to 7.4 per node at apex, Thorn shape is straight and needle-like, (the length of the thorn is greater than four times its diameter) and length is approximately 4 mm (FIG. 2). 'Jaclyn' thorn color is purple-red (Royal Horticultural Society color plate No. 183C) in color throughout; however, the coloration is less intense as it extends in a circle another 1 mm into the surrounding cane, resembling Royal Horticultural Society color plate No. 182C. The upper surfaces of leaves are dark green, most closely inhue to Royal Horticultural Society Color Plate No. 143 B or C, depending on the amount of N fertilization and time of season, senescing leaves have a green yellow color resembling Royal Horticultural Society color plate No. 146A. The lower surface of 'Jaclyn' leaves is pubescent grey-green resembling Royal Horticultural Society color plate No. 191 C (FIG. 3). Leaves are primarily trifoliolate and average 14 cm from the distal end of the petiole to the distal end of the terminal leaflet. The basal leaflets average 20 cm from terminal point to point. The ratio the petiole length to petiolule (the leaf stalk on the apical leaflet only) is 2.25 to 1, with petiole average length of 5 cm. Lateral leaflets are sessile and join at the petiole apex with the apical leaf petiolule (FIG. 3). Leaf serration, laminar puckering and veination pattern are common for most cultivars of red raspberry and cannot be used to distinguish this cultivar.

Figure 4:
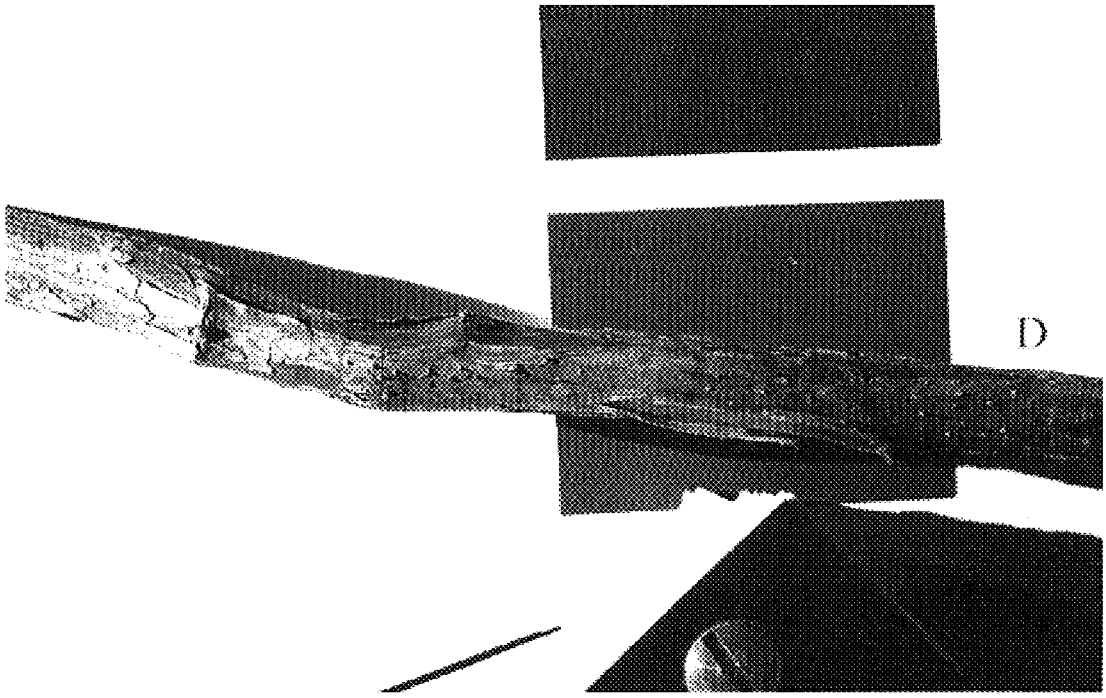
FIG. 4 shows the base of a mature floricane in mid-November with Royal Horticultural Society color plate No. 202D.

Leaves abscise readily in October and November and coloration changes and exfoliation indicative of the change to a floricane occurs in October and November. 'Jaclyn' floricanes are brown in color, resembling in hue Royal Horticultural Society color plate No. 200D, but varying in color intensity (FIG. 4). Floricanes exfoliate to a moderate amount (FIG. 4). No overwintering has been attempted with this fall bearing cultivar as few nodes are left after primocane fruit is produced.

Figure 5:
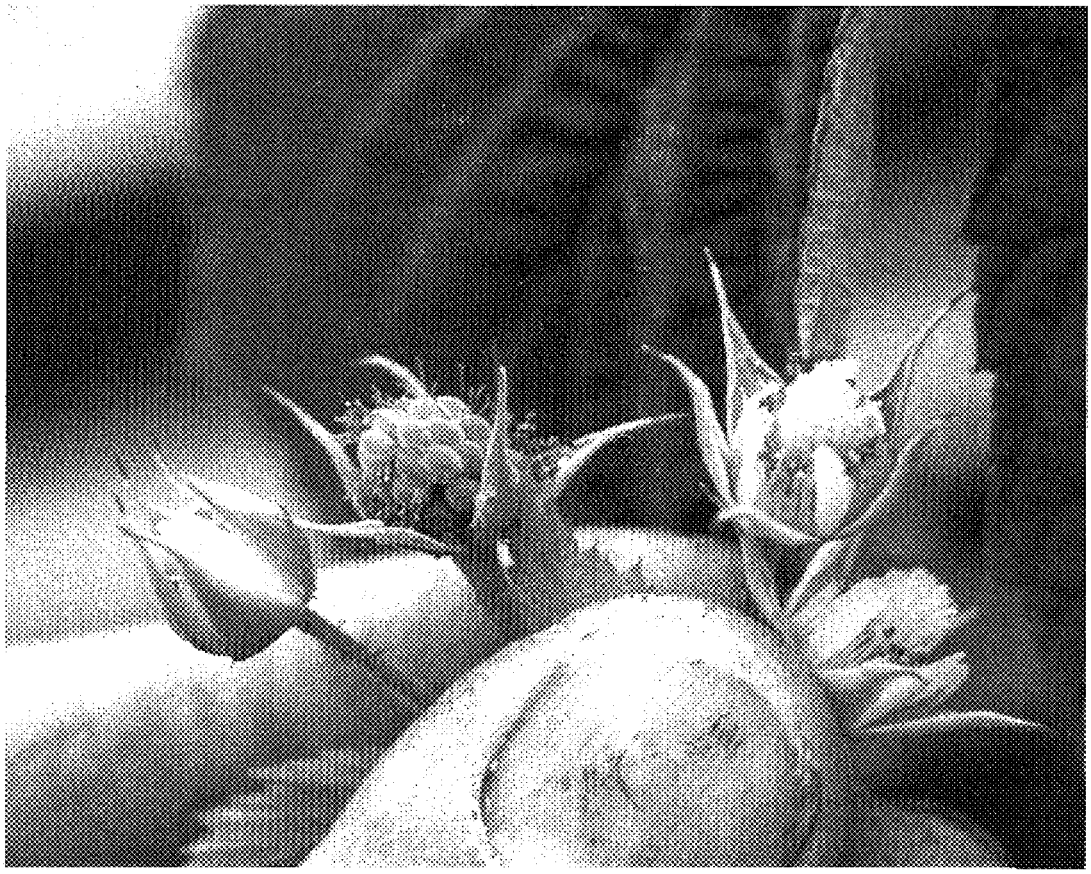
FIG. 5 shows development of 'Jaclyn' flowers and an immature fruit.
Figure 6:
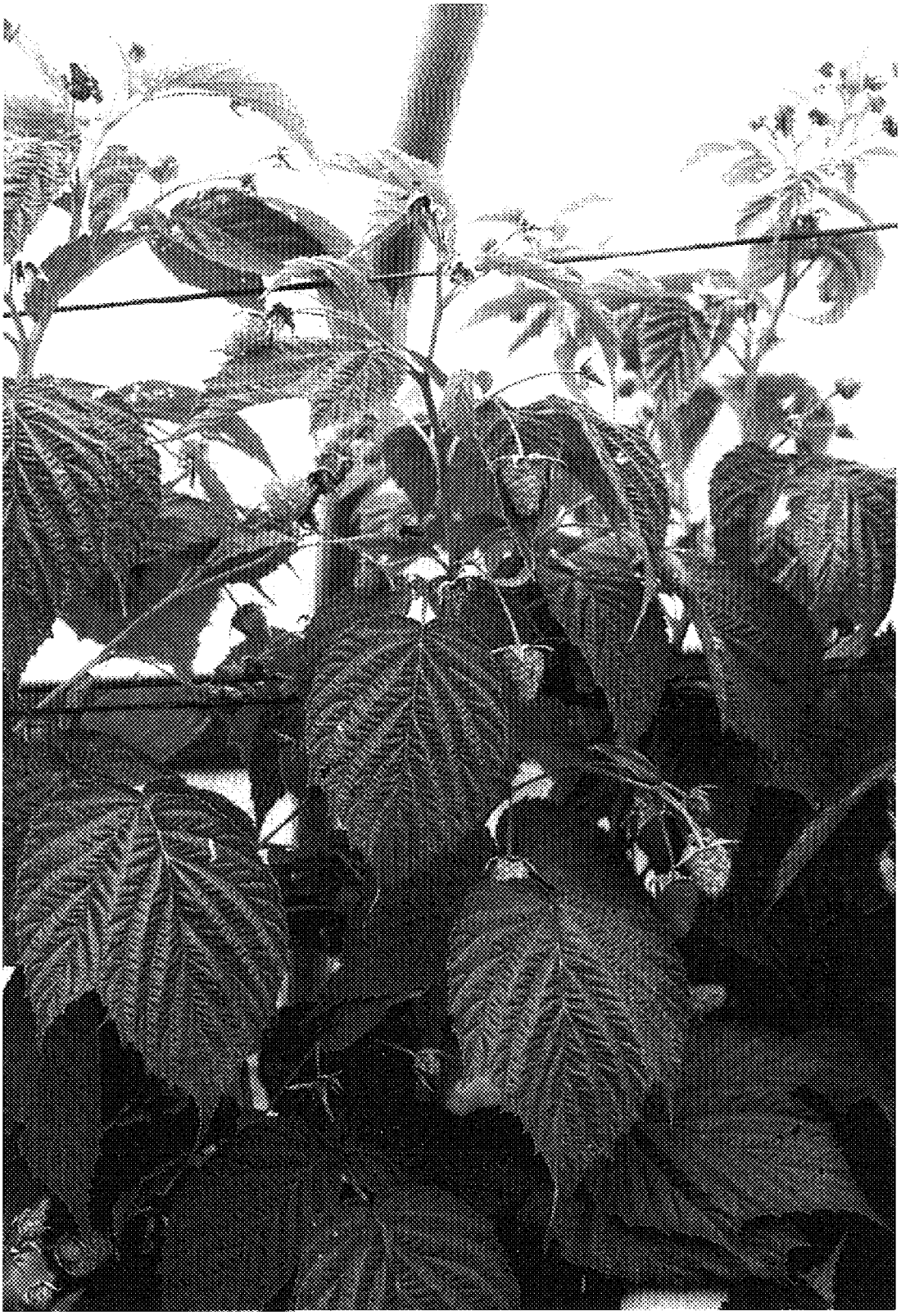
FIG. 6 shows a primocane fruiting cluster of 'Jaclyn' in mid July, 2002, showing the exposure of 'Jaclyn' fruit as grown in an unheated tunnel.

Flowers appear after 14.7 nodes, on average, on adult plant 'Jaclyn' primocane or after 21.2 nodes on tissue culture produced plant, first year primocanes. By comparison, adult 'Heritage' and 'Josephine' primocanes flower, on average, after 28.5 and 35.8 nodes respectively. The unscented flower morphology and early fruit morphology is typical of most red raspberry cultivars, five white 0.5 cm long petals (Royal Horticultural Society color plate No. 155D) which abscise after pollination, five 0.9 cm long grey green sepals (Royal Horticultural Society color plate No. 194B), 110 pistils on early fruit to 70 on later fruit and over 70 anthers; none of these traits can be used to identify 'Jaclyn' (see FIG. 5). Flower trusses are typical cymose clusters averaging 48.4 flowers per cane (see FIG. 6).

Figure 7:
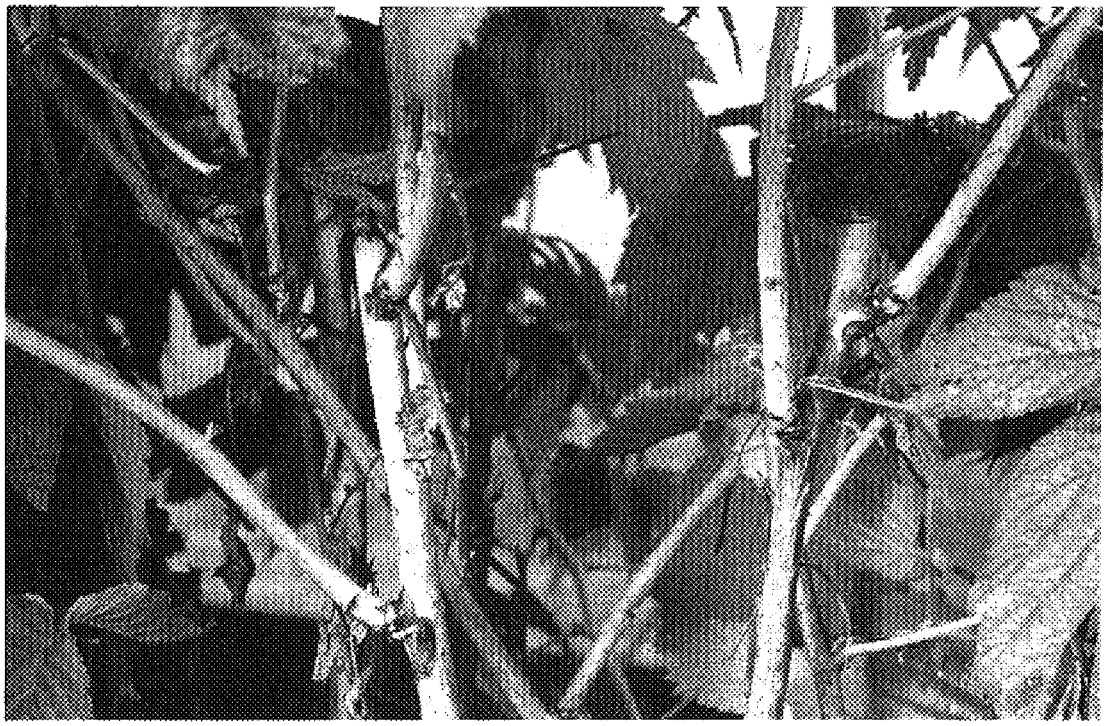
FIG. 7 shows resprouting of flower trusses basal to the primocane fruiting zone.

Fruit is borne on 41 to 44% of the total nodes of the primocanes; the proportion of cane producing fruit is greater than 'Heritage' (27%), 'Caroline' (29%) or 'Josephine' (21%) and, by observation in other fields, this proportion in 'Jaclyn' is also greater than that of 'Anne' (U.S. Plant Pat. No. 10,411), 'Autumn Bliss' (U.S. Plant Pat. No. 6,597), 'Autumn Britton' (unpatented), 'Amity' (unpatented) or 'Ruby' (U.S. Plant Pat. No. 7,067). The number of nodes producing fruit includes 7% of the nodes (on average 2 nodes per cane) which break bud and produce trusses after the apical nodes have fruited (FIG. 7). Resprouting of floral buds subtending the main truss occurs within two weeks of 95% harvest of the main crop when the top is pruned promptly after the last commercial harvest. Resprouting is delayed for one to two weeks if the plant is unpruned. If the growing season is sufficient (>3500 growing degree days base 50F), this crop will ripen in October. A third crop will appear after, and basal to, the second crop but this occurs without frost damage only in heated tunnels or greenhouses.

Figure 8:
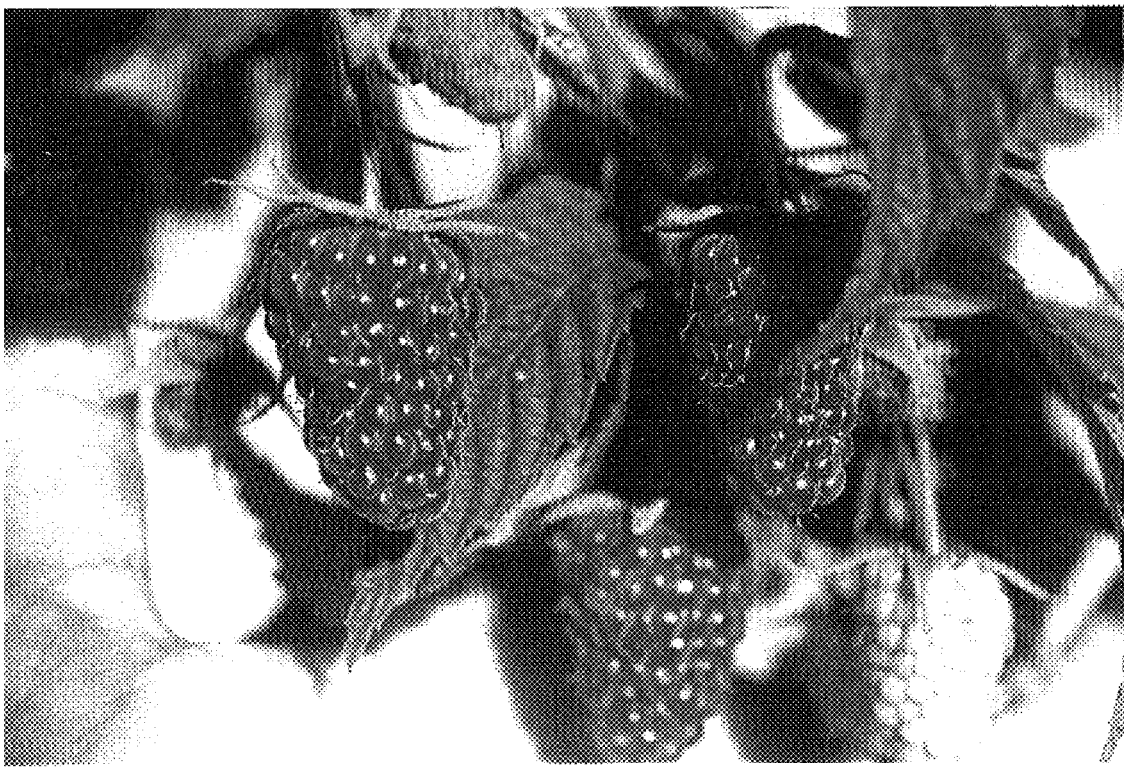
FIG. 8 shows the initial primocane fruit of 'Jaclyn'

Fruit are easily distinguishable by long conic shape for this variety at 12 days post pollination. 'Jaclyn' fruit are very symmetrical. Fruit will tear across the drupelets rather than separate from each other, that is, the fruit does not shatter under pressure of hand harvest. It is common to observe perfectly curvilinear rows of drupelets, i.e. along the latitudinal circumference of the fruit (FIG. 8). In Colt's Neck, N.J. in 2002, when 19 of the 30 days during flowering and initial fruit growth were higher than 90 F (32C), the initial mature fruit length was 2.4 cm, while width was 1.8 cm, producing a ratio of 4:3, which becomes closer to 1:1 on later fruit. Early fruit have 105 drupelets, and average 3.1 grams fresh weight. Later fruit are smaller and average 65 drupelets; this is a relatively small variation in fruit size over the season. Overall fruit weight in central N.J. in 2002 is 2.48 grams, compared to 1.55 g for 'Heritage' and 2.75 g for 'Josephine'.

Fruit ripens 23 days after pollination on primocanes in New Jersey. Fruit is ripe beginning early July to late July in the Mid-Atlantic region. In Colt's Neck, N.J., the 5%, 50% and 95% ripe dates were: 'Jaclyn'—July 28, August 14 and September 23 respectively. For 'Heritage' the ripeness dates were: August, 13 August 30 and September 27. For 'Josephine' the ripeness dates were: September, 7 October 5 and October 26 (last frost October 29). In Mt. Airy, Md. in 2002, when grown in an unheated tunnel, the initial primocane fruit were ripe from July 10 to August 30. These ripeness periods are similar to 'Polana' (unpatented), which is 7–16 days earlier than 'Heritage' in Iowa, but 4–7 days earlier than 'Caroline' (U.S. Plant Pat. No. 10,412), 'Autumn Bliss' (U.S. Plant Pat. No. 6,597), 'Autumn Britton' (unpatented). Other primocane fruiting cultivars, like 'Ruby' (U.S. Plant Pat. No. 7,067) and 'September' (unpatented) and 'Josephine' (U.S. Plant Pat. No. 12,350) are over a month later to ripen than 'Jaclyn'.

Figure 9:
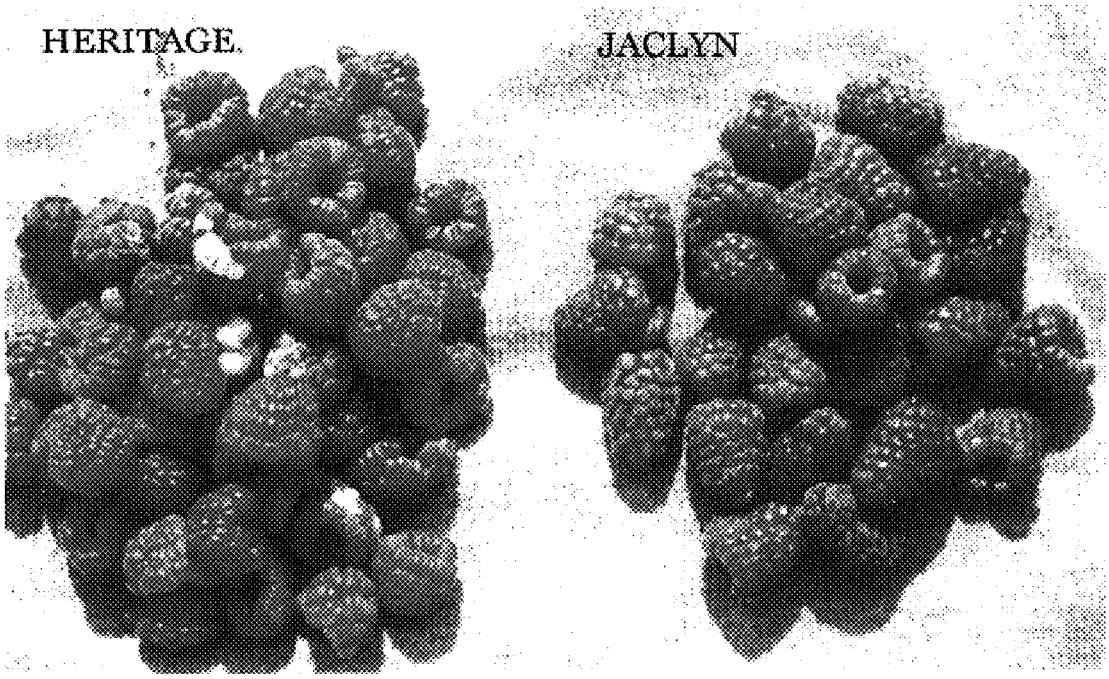
FIG. 9 shows the lack of sunscalding of late season 'Jaclyn' fruit compared to early season 'Heritage' fruit (on the left). Late season 'Heritage' fruit ripened in cooler weather, with shorter days.
Figure 10:
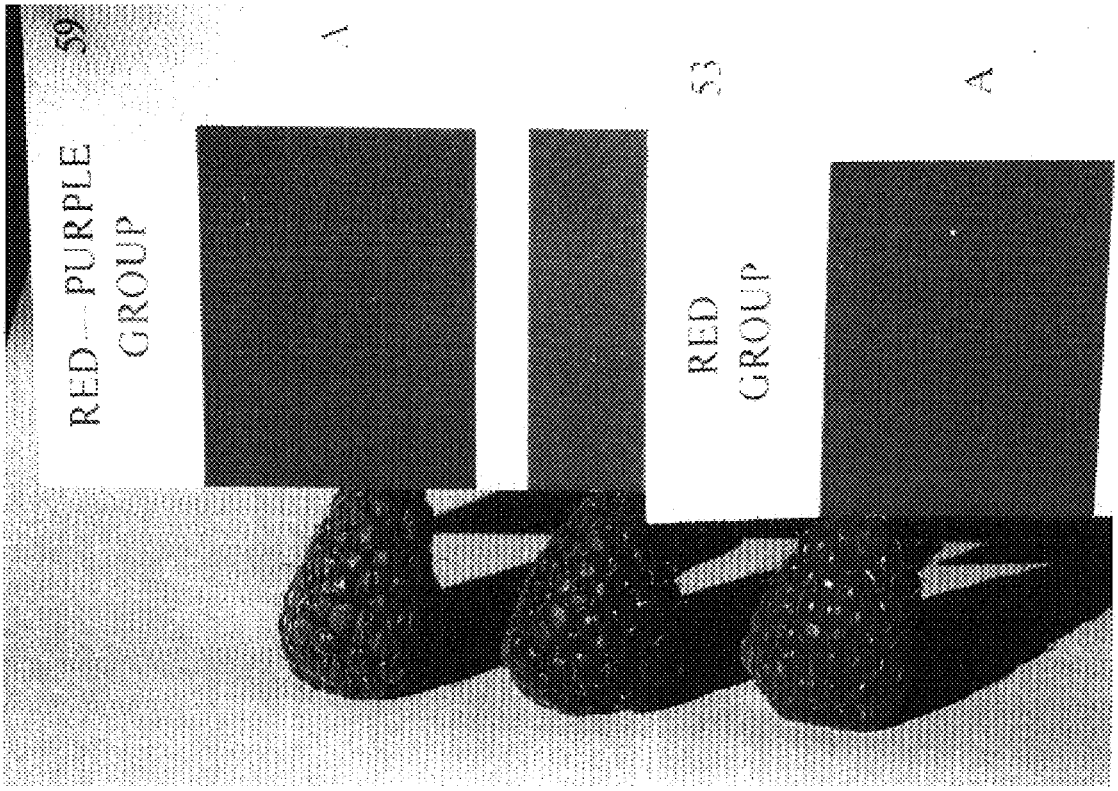
FIG. 10 shows the darker color of "Jaclyn" fruit either as fully ripe fruit or after 7 days of storage in a 40 F. refrigerator and Royal Horticultural Society color plates No. 59A and 53A.

'Jaclyn' fruit are dark red when ripe, closely resembling the hue of Royal Horticultural Society color plate No. 53A (see FIG. 9). When fully or over ripe, or upon 7 days storage, fruit develops a purple red color, resembling Royal Horticultural Society color plate No. 59A. Fruit have an insignificant amount observable pubescence, typical of most other commercial cultivars, but noticeably less than 'Josephine'. Drupelets are held together tightly. The collar is very uniform. The cavity width is 30% of the diameter of the fruit, typically 0.6 cm in diameter on the initial fruit. The fruit readily separates from the plant's recepticle in warm conditions, but is difficult to remove when ripened in colder weather (<65F). This is partly due to the long recepticle to fruit interface. The fruit does not break down after at least one week of storage in ventilated plastic, pint-sized "clam shells" in a common household refrigerator. The temperature of the refrigerator averaged 40F. Humidity was maintained at 90% by adjusting the cold room which surrounded the refrigerator. The fruit has less fruit rot and sunscald than the standard fall bearing cultivars ('Heritage' (unpatented) (see FIG. 10), 'Autumn Bliss' (U.S. Plant Pat. No. 6,597), 'Caroline' (U.S. Plant Pat. No. 10,412) and 'Polana' (unpatented). Flavor is sweet and the aroma is strong and characteristic of red raspberry. The texture of the fruit is firmer than other eastern US-grown red raspberry cultivars known to us, with the exceptions of 'Tulameen' (not patented) and 'Emily' floricane fruiters and 'Josephine', a primocane fruiter. 'Jaclyn' fruit is suitable for limited shipment; however, because it extends the season, it would be especially useful for local farm market situations where the grower has no options, such as growing in different locations, to produce an earlier crop. 'Jaclyn' fruit has sufficient flavor to benefit a pick-your-own marketing operation.

The plant is field resistant to many of the common insect pests, especially potato leaf hopper, and diseases in the eastern United States, e.g. mildew, anthracnose and verticillium wilt. The plant is very susceptible to late season leaf rust (yellow rust) in the mid-Atlantic states. Outdoors, rust defoliates the lower canes of plants, especially when crop load is high. The plant's reaction to *Phyophthora fragarae* root rot is probably moderately resistant, based on field reaction, not on controlled testing. Fruit is usually free from rot in the field, more so than 'Anne' and 'Caroline', but not 'Josephine'.

FRUIT PRODUCTION

'Jaclyn' has been tested in a replicated trial in Colt's Neck, N.J. The following data were collected in the summer and fall of 2002. Plants were planted in July, 1997, the data below could be classified as a mature plant yield. The summer of 2002 was characterized by above normal temperatures, but much below normal rainfall. Total yield per acre on primocanes was: 9395, 6105 and 2303 lbs for 'Jaclyn', 'Heritage' and 'Josephine' respectively. In Mt. Airy, Md. in 2002, at 5 ft spacing between rows, yield was 9540 lbs per acre; however, in a more crowded 3 ft spacing, yield was reduced to 5796 lbs per acre.

'Jaclyn' has been asexually reproduced at the University of Maryland by tissue culture, dormant cuttings and mist-propagated root sucker cuttings for five years. Suckering is moderate to high and the plant readily establishes either in culture or in a mist rooting chamber. Such propagules maintain the distinctive characteristics of 'Jaclyn', including earliness to fruit and definitive fruit quality traits including sunscalding resistance. Thus, the observed plant retains its distinctive characteristics and reproduces true to type in successive generations.

What is claimed:

1. A new and distinct fall bearing red raspberry plant known as 'Jaclyn' as described herein, illustrated and identified by the characteristics set forth above.

* * * * *